United States Patent
Xia et al.

(10) Patent No.: US 6,309,658 B1
(45) Date of Patent: Oct. 30, 2001

(54) TREATMENT OF CONTACT LENSES WITH AQUEOUS SOLUTION COMPRISING A CARBONATE SALT FOR ENHANCED CLEANING

(75) Inventors: Erning Xia, Penfield; Lisa C. Simpson, Rochester; John Denick, Jr., Pittsford, all of NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/190,790

(22) Filed: Nov. 12, 1998

Related U.S. Application Data

(60) Provisional application No. 60/065,511, filed on Nov. 12, 1997.

(51) Int. Cl.[7] ............................. A01N 25/00; A61K 9/00; A61K 31/155

(52) U.S. Cl. ............................ 424/405; 424/429; 514/635

(58) Field of Search ................................. 424/405, 78.04, 424/429; 422/28; 514/635

(56) References Cited

U.S. PATENT DOCUMENTS

| | | | |
|---|---|---|---|
| 4,758,595 | 7/1988 | Ogunbiyi | 514/635 |
| 4,836,986 * | 6/1989 | Ogunbiyi et al. | 422/28 |
| 6,143,244 * | 11/2000 | Xia et al. | 422/28 |

FOREIGN PATENT DOCUMENTS

| | | | |
|---|---|---|---|
| 0 437 179 A2 | 12/1990 | (EP) | C11D/3/04 |
| 1432345 | 4/1976 | (GB) . | |
| WO 97/00931 | 1/1997 | (WO) | C11D/3/37 |

* cited by examiner

*Primary Examiner*—Thurman K. Page
*Assistant Examiner*—Blessing Fubara
(74) *Attorney, Agent, or Firm*—Robert B. Furr, Jr.; Denis A. Polyn

(57) ABSTRACT

The present invention provides methods and compositions for cleaning and disinfecting contact lenses, which compositions comprise a carbonate or bicarbonate salt, a non-carbonate buffer system, an antimicrobial agent, and a non-ionic surfactant. Products according to the present invention, especially multi-purpose solutions, provide simultaneous disinfection and cleaning of contact lenses including the prevention or removal of protein and lipid deposits and other debris.

18 Claims, No Drawings

TREATMENT OF CONTACT LENSES WITH AQUEOUS SOLUTION COMPRISING A CARBONATE SALT FOR ENHANCED CLEANING

This application claims benefit to Provisional Application 60/065,511 filed Nov. 12, 1997.

FIELD OF THE INVENTION

The present invention is directed toward methods for treating contact lenses and compositions for the same, including an alkali metal salt of carbonate for enhanced cleaning.

BACKGROUND

Generally, contact lenses in wide use fall into three categories: (1) hard lenses formed from materials prepared by polymerization of acrylic esters, such as polymethyl methacrylate (PMMA), (2) rigid gas permeable (RGP) lenses formed from silicone acrylates and fluorosilicone methacrylates, and (3) gel, hydrogel or soft type lenses. The hard and rigid-type lenses, because they are characterized by low vapor diffusion and absorb only minor amounts of aqueous fluids, have a lower tendency to bind ingredients used in contact-lens care solutions. On the other hand, soft lenses have a greater tendency to bind active ingredients in contact-lens solutions and, therefore, it is especially challenging to develop solutions designed for the treatment of soft-type lenses, whether made from the more traditional copolymers of 2-hydroxyethylene methacrylate (HEMA) or from the newer silicon-containing hydrogel materials.

In the normal course of wearing contact lenses, tear film and debris consisting of proteinaceous, oily, sebaceous, and related organic matter have a tendency to deposit and build up on lens surfaces. Many factors influence deposit formation, including patient to patient variation, lens material, care regimen, and environment. In general, high water, ionic lens materials absorb more protein than low water or non-ionic lens materials. As part of the routine care regimen, contact lenses must be cleaned to remove these tear film deposits and debris. If these deposits are not properly removed, both the wettability and optical clarity of the lenses are substantially reduced and wearer discomfort may result.

Further, contact lenses must also be disinfected to kill harmful microorganisms that may be present or grow on the lenses. Some of the most popular products for disinfecting lenses are multi-purpose solutions that can be used to clean, disinfect and wet contact lenses, followed by direct insertion (placement on the eye) without rinsing. Obviously, the ability to use a single solution for contact-lens care is an advantage. Such a solution, however, must be particularly gentle to the eye, since at least some of the solution will be on the lens when inserted and will come into contact with the eye.

British Patent No. 1,432,345 discloses contact lens disinfecting compositions containing a polymeric biguanide and a mixed phosphate buffer. Compositions as disclosed by this patent, however, have corneal staining values of 17% or more, far above that which is desirable for patient acceptability.

U.S. Pat. No. 4,758,595 to Ogunbiyi et al. disclosed that a contact-lens solution containing a polyaminopropyl biguanide (PAPB), also known as polyhexamethylene biguanide (PHMB), has enhanced efficacy when combined with a borate buffer. These disinfecting and preservative solutions are especially noteworthy for their broad spectrum of bactericidal and fungicidal activity at low concentrations coupled with very low toxicity when used with soft-type contact lenses. Compositions containing PHMB and borate have been commercialized in various products including multi-purpose solutions, at levels of about 1 ppm or less for use with soft contact lenses.

The fact that multi-purpose solutions are designed for use as a wetting agent, without rinsing, means that the solution must be ophthalmically safe for eye contact. This limits, to some extent, the type and concentration of both cleaning agents and biocides that can be employed in the solution. For example, as can be readily understood, biocides or cleaners in a shampoo product may not be suitable for ophthalmic use. A challenge has been to develop a formula that is, on the one hand, maximally efficacious and, on the other hand, sufficiently gentle to be not only safe, but comfortable for in-the-eye use.

With conventional contact-lens cleaners or disinfectants, including multi-purpose solutions, lens wearers typically need to digitally or manually rub the contact lenses (typically between a finger and palm or between fingers) during treatment of the contact lenses. The necessity for the daily "rubbing" of contact lenses adds to the time and effort involved in the daily care of contact lenses. Many contact-lens wearers dislike having to perform such a regimen or consider it to be an inconvenience. Some wearers may be negligent in the proper "rubbing" regimen, which may result in contact-lens discomfort and other problems. Sometimes rubbing, if performed too rigorously, which is particularly apt to occur with begining lens wearers, may damage the lenses. This can be problematic when a replacement lens is not immediately available.

Contact lens solutions that qualify as a "Chemical Disinfecting Solution" do not require rubbing to meet biocidal performance criteria (for destroying representative bacteria and fungi) set by the US Food and Drug Administration (FDA) under the Premarket Notification (510k) Guidance Document For Contact Lens Care Products, May 1, 1997. In contrast, a contact-lens solution, referred to as a "Chemical Disinfecting System," not qualifiing as a Chemical Disinfecting Solution, requires a rubbing regimen to pass biocidal performance criteria. Traditionally, multi-purpose solutions (used for disinfecting and wetting or for disinfecting, cleaning, and wetting) have qualified as a Chemical Disinfecting System, but not as a Chemical Disinfecting Solution.

Traditional contact-lens solutions may depend on the rubbing regimen, not only for efficacious disinfection, but for efficacious cleaning. Thus, in order to develop a contact-lens care solution that would provide efficacious cleaning without a rubbing regimen for cleaning would require improved cleaning while still being sufficiently gentle for in-the-eye use.

It would be desirable to obtain a multi-purpose contact-lens solution that would provide increased cleaning efficacy. It would be desirable to obtain such improved cleaning efficacy while (1) maintaining the biocidal efficacy of the product and (2) maintaining a low order of toxicity to eye tissue, such that after the solution is used to treat a contact lens, the lens can subsequently be placed on the eye without rinsing the solution from the lens. While still more challenging to develop, it would also be desirable to obtain a solution that exhibits both efficacious cleaning and disinfecting of a contact lens, without requiring a rubbing regimen, or at least not inherently or invariably requiring it for acceptable performance, and which solution would still allow direct placement of the contact lens on an eye following soaking in the solution and/or rinsing and rewetting with the solution.

SUMMARY OF THE INVENTION

The present invention is directed to a biguanide-containing disinfecting solution exhibiting enhanced cleaning efficacy. The present invention includes methods for treating contact lenses and compositions for the same. The present invention includes contacting a lens with an aqueous solution comprising:

(1) 0.010 to 1.0 percent by weight of the solution of an alkali metal carbonate or bicarbonate; and (2) an effective amount of a buffering system comprising one or more non-carbonate buffers having a buffering capacity of 0.01 to 0.5 mM of 0.01 N of HCl and 0.01 to 0.3 of 0.01 N of NaOH to change the pH one unit;

(3) an effective amount of a non-ionic surfactant; and (4) an effective amount of at least one germicide.

The method of the present invention comprises cleaning and disinfecting a contact lens with the above-described solution. Products according to the present invention provide enhanced cleaning, including significant improvement in lipid cleaning. In one embodiment of the present invention, the subject lens-care solution disinfects and cleans a contact lens in a no-rub regimen. As such, the present invention can offers significant advantages over known cleaning and disinfecting regimens.

DETAILED DESCRIPTION OF THE INVENTION

The present invention can be used with all contact lenses such as conventional hard, soft, rigid and soft gas permeable, and silicone (including both hydrogel and non-hydrogel) lenses, but is especially useful for soft lenses. By the term "soft lens" is meant a lens having a proportion of hydrophilic repeat units such that the water content of the lens during use is at least 20% by weight. The term "soft contact lens" as used herein generally refers to those contact lenses which readily flex under small amounts of force. Typically, soft contact lenses are formulated from polymers having a certain proportion of repeat units derived from hydroxyethyl methacrylate and/or other hydrophilic monomers, typically crosslinked with a crosslinking agent. However, newer soft lenses, especially for extended wear, are being made from high-Dk silicone-containing materials.

The present invention is useful for contact-lens care solutions, including disinfecting solutions and/or cleaning solutions, especially those that also qualify as a multi-purpose solution. A disinfecting solution is generally defined as a contact-lens care product containing one or more active ingredients (for example, anti-microbial agents and/or preservatives) in sufficient concentrations to destroy harmful microorganisms on the surface of a contact lens within the recommended minimum soaking time. The recommended minimum soaking time is included in the package instructions for use of the disinfecting solution. The term "disinfecting solution" does not exclude the possibility that the solution may also be useful as a preserving solution, or that the disinfecting solution may also be useful for other purposes such as daily cleaning, rinsing and storage of contact lenses, depending on the particular formulation. The present solution, in combination with its container or bottle and packaging, including instructions for use in accordance with a specified regimen, may be considered a novel and improved kit, package, or system for the care of contact lenses.

A solution that is useful for cleaning, disinfecting, storing, and rinsing a contact lens, particularly soft contact lenses, is referred to herein as a "multi-purpose solution." Multi-purpose solutions do not exclude the possibility that some wearers, for example, wearers particularly sensitive to chemical disinfectants or other chemical agents, may prefer to rinse or wet a contact lens with another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis. By the term "cleaning" is meant that the solution contains one or more cleaning agents in sufficient concentrations to loosen and remove loosely held lens deposits and other contaminants on the surface of a contact lens, especially if used in conjunction with digital manipulation (for example, manual rubbing of the lens with a solution) or with an accessory device that agitates the solution in contact with the lens, for example, a mechanical cleaning aid. The critical micelle concentration of a surfactant-containing solution is one way to evaluate its cleaning effectiveness.

Traditionally, multi-purpose solutions on the market require a regimen involving mechanical rubbing of the contact lens with the multi-purpose solution, in order to provide the required disinfection and cleaning. Such a regimen is required under governmental regulatory authorities (for example, the FDA or Food & Drug Administration in the USA) for a Chemical Disinfection System that does not qualify as a Chemical Disinfecting Solution. In one embodiment of the present invention, it is possible to formulate a cleaning and disinfecting product that, on the one hand, is gentle enough to be used as a wetting agent and, on the other hand, is able to provide improved cleaning and disinfection in the absence of a rubbing regimen. For example, a product qualifying as a Chemical Disinfecting Solution must meet biocidal performance criteria established by the US FDA for Contact Lens Care Products (May 1, 1997) which criteria does not involve rubbing of the lenses. In one embodiment of the present invention, a composition is formulated to meet the requirements of the FDA or ISO Stand-Alone Procedure for contact lens disinfecting products. Similarly, compositions of the present invention can be formulated to provide enhanced cleaning without the use of a rubbing regimen. Such formulations may ensure higher patient compliance and greater universal appeal than traditional disinfecting, or multi-purpose disinfecting and cleaning, products.

The solutions according to the present invention are physiologically compatible. Specifically, the solution must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO (International Standards Organization) standards and U.S. FDA (Food & Drug Administration) regulations. The solution should be sterile in that the absence of microbial contaminants in the product prior to release must be statistically demonstrated to the degree necessary for such products.

As previously indicated, the present invention includes an aqueous solution comprising a disinfecting agent, a buffering system, a non-ionic surfactant, and a carbonate or bicarbonate salt in the amount of 0.010 to 1.0 percent by weight of the total composition (solution), preferably 0.05 to 0.2 weight percent, most preferably 0.08 to 0.12 weight percent.

Suitably, the carbonate or bicarbonate salt is an alkali metal salt, including, for example, sodium bicarbonate, sodium carbonate, potassium carbonate, potassium bicarbonate, and mixtures thereof. The most preferred carbonates are sodium carbonate and sodium bicarbonate.

The present invention includes a non-carbonate buffering system that has a buffering capacity of 0.01 to 0.5 mM, preferably 0.03 to 0.45, of 0.01 N of HCl and 0.01 to 0.3, preferably 0.025 to 0.25, of 0.01 N of NaOH to change the pH one unit. By the term "non-carbonate buffering system" is meant that the buffer system comprises compounds or buffers other that carbonate or bicarbonate salts that provide the indicated buffer capacity which buffer capacity is measured in a solution containing only the buffer system.

The pH of the present solutions should be maintained within the range of 5.0 to 8.0, more preferably about 6.0 to 8.0, most preferably about 6.5 to 7.8. By the terms "buffer" or "buffer substance" is meant a compound that, usually in combination with at least one other compound, provides a buffering system in solution that exhibits buffering capacity, that is, the capacity to neutralize, within limits, either acids or bases with relatively little or no change in the original pH. The term "buffering capacity" is defined to mean the millimoles (mM) of strong acid or base (or respectively, hydrogen or hydroxide ions) required to change the pH by one unit when added to one liter (a standard unit) of the buffer solution. From this definition, it is apparent that the smaller the pH change in a solution caused by the addition of a specified quantity of acid or alkali, the greater the buffer capacity of the solution. See, for example, *Remington: The Science and Practice of Pharmacy*, Mack Publishing Co., Easton, Penn. (19th Edition 1995), Chapter 17, pages 225–227. The buffer capacity will depend on the kind and concentration of the buffer components. The buffer capacity is measured from a starting pH of 6 to 8, preferably from 7.4 to 8.4.

Buffering systems include but are not limited to the combination of a weak acid and the salt of the weak acid (the so-called conjugate base). Borate buffers include, for example, boric acid and its salts, for example, sodium borate or potassium borate. Borate buffers also include compounds such as potassium tetraborate or potassium metaborate that produce borate acid or its salt in solutions. Phosphate buffers include, for example, phosphoric acid and its salts, for example, phosphate buffers (including combinations of $M_2HPO_4$, $MH_2PO_4$ and $MH_2PO_4$, wherein M is independently a alkali metal salt such as K and Na). The term phosphate includes compounds that produces phosphoric acid or its salt in solution.

Other buffer substances may be used in the composition. For example, traditionally known buffers include, for example, citrates, citric acid, TRIS, and the like. Other ingredients in the solution, while having other functions, may also affect the buffer capacity. For example, EDTA, often used as a sequestrant, may have a noticeable effect on the buffer capacity of a composition. Generally, buffers will be used in amounts ranging from about 0.05 to 2.5 percent by weight, and preferably, from 0.1 to 1.5 percent.

Borate buffers, either all-borate buffers or combined with other buffers, are preferred, especially for use with biguanide disinfecting agents, since borate buffers are known for enhancing the efficacy of polymeric biguanides. For example, U.S. Pat. No. 4,758,595 to Ogunbiyi et al. discloses that a contact-lens solution containing a polyaminopropyl biguanide (PAPB), also known as polyhexamethylene biguanide (PHMB), has enhanced efficacy when combined with a borate buffer. Applicants have found that borate buffers also enhance the efficacy of biguanides in general, including bis(biguanides) such as alexidine.

An especially preferred buffer system is the combination of borate and a phosphate buffer, for example, boric acid and mono and/or dibasic phosphate salt such as sodium and/or disodium phosphate. An alternate buffer system, for example, are the combination of sodium borate and phosphoric acid or the combination of sodium borate and the monobasic phosphate. For example, a solution may comprise about 0.05 to 2.5% by weight of a phosphoric acid or its salt and 0.1 to 5.0% by weight of boric acid or its salt. In such a borate-phosphate buffer, the phosphate buffer is suitably used (in total) at a concentration of 0.004 to 0.2 M (Molar), preferably 0.04 to 0.1 M, and the borate buffer (in total) is suitably used at a concentration of 0.02 to 0.8 M, preferably 0.07 to 0.2 M.

In addition to buffering agents, in some instances it may be desirable to include sequestering agents in the present solutions in order to bind metal ions which might otherwise react with the lens and/or protein deposits and collect on the lens. Ethylene-diaminetetraacetic acid (EDTA) and its salts (disodium) are examples. They are usually added in amounts ranging from about 0.01 to about 0.2 weight percent. Other suitable sequestering agents include gluconic acid, citric acid, tartaric acid and their salts, e.g. sodium salts. Preferred sequestering agents, which are also effective for removing protein deposits, are the phosphonate compounds represented by the following Formula (I):

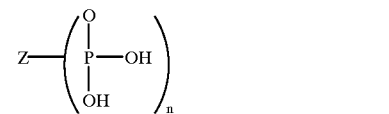

wherein Z is a connecting radical equal in valence to n, wherein n is an integer from 1 to 6, preferably 1 to 3. Such phosphonate compounds are disclosed in WO 97/31659. The subject aqueous solution suitably includes at least 0.003 percent weight by volume of the subject phosphonic compound in the total solution, preferably 0.005 to 2.5 percent weight by volume and more preferably about 0.01 to 0.5 percent weight by volume in the total solution.

Typically, the aqueous solutions of the present invention for treating contact lenses are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation. Examples of suitable tonicity adjusting agents include, but are not limited to: sodium and potassium chloride, dextrose, glycerin, calcium and magnesium chloride. These agents are typically used individually in amounts ranging from about 0.01 to 2.5% (w/v) and preferably, form about 0.2 to about 1.5% (w/v). Preferably, the tonicity agent will be employed in an amount to provide a final osmotic value of 200 to 450 mOsm/kg and more preferably between about 250 to about 350 mOsm/kg, and most preferably between about 280 to about 320 mOsm/kg.

The subject solution includes at least one antimicrobial agent, preferably a biguanide compound or polymer. Representative biguanides are the bis(biguanides), such as alexidine or chlorhexidine or salts thereof, and polymeric biguanides such as polymeric hexamethylene biguanides (PHMB), and combinations thereof. Polymeric biguanides, and water-soluble salts thereof, having the following formula:

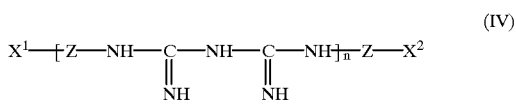

wherein Z is an organic divalent bridging group which may be the same or different throughout the polymer, n is on average at least 3, preferably on average 5 to 20, and $X^1$ and $X^2$ are independently selected from the groups.

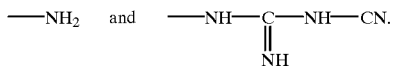

One preferred group of water-soluble polymeric biguanides will have number average molecular weights of at least 1,000 and more preferably will have number average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. No. 3,428,576 describes the preparation of polymeric biguanides from a diamine and salts thereof and a diamine salt of dicyanimide.

Most preferred are the polymeric hexamethylene biguanides, commercially available, for example, as the hydrochloride salt from Zeneca (Wilmington, Del.) under the trademark Cosmocil™ CQ. Such polymers and water-soluble salts are referred to as polyhexamethylene (PHMB) or polyaminoptopyl biguanide (PAPB). The term polyhexamethylene biguanide, as used herein, is meant to encompass one or more biguanides have the following formula:

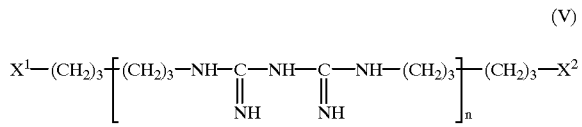

wherein $X^1$ and $X^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated herein by reference. Preferably, the water-soluble salts are compounds where n has an average value of 2 to 15, most preferably 3 to 12.

In one preferred embodiment, a polymeric biguanide is used in combination with a bis(biguanide) compound. Polymeric biguanides, in combination with bisbiguanides such as alexidine, are effective in concentrations as low as 0.00001 weight percent (0.1 ppm). It has also been found that the bactericidal activity of the solutions may be enhanced or the spectrum of activity broadened through the use of a combination of such polymeric biguanides with alexidine or similar biguanide, as disclosed in commonly assigned copending application U.S. Ser. No. 09/190,899 filed on the even date herewith.

An optional non-biguanide disinfectant/gennicide can be employed as a solution preservative, but it may also function to potentiate, complement or broaden the spectrum of microbiocidal activity of another germicide. This includes microbiocidally effective amounts of germicides which are compatible with and do not precipitate in the solution, in concentrations ranging from about 0.00001 to about 0.5 weight percent, and more preferably, from about 0.0001 to about 0.1 weight percent. Suitable complementary germicidal agents include, but are not limited to, quaternary ammonium compounds or polymers, thimerosal or other phenylmercuric salts, sorbic acid, alkyl triethanolamines, and mixtures thereof. Representative examples of the quaternary ammonium compounds are compositions comprised of benzalkonium halides or, for example, balanced mixtures of n-alkyl dimethyl benzyl ammonium chlorides. Other examples include polymeric quaternary ammonium salts used in ophthalmic applications such as poly [(dimethyliminio)-2-butene-1,4-diyl chloride], [4-tris(2-hydroxyethyl) ammonio]-2-butenyl-w-[tris(2-hydroxyethyl) ammonio]dichloride (chemical registry number 75345-27-6) generally available as polyquaternium 1 ® from ONYX Corporation. Novel Polyquaterniums are disclosed in copending application U.S. Ser. No. 09/190,509 (docket no. 6,153,568 P01587) filed on even date herewith.

The acid-addition salts of the germicides used in the present composition may be derived from an inorganic or organic acid. In most circumstances it is preferable that the salts be derived from an acid which is readily water soluble and which affords an anion which is suitable for human usage, for example a pharmaceutically-acceptable anion. Examples of such acids are hydrochloric, hydrobromic, phosphoric, sulphuric, acetic, D-gluconic, 2-pyrrolidino-5-carboxylic, methanesulphonic, carbonic, lactic and glutamic acids. The hydrochloride salt is preferred.

In the present application, the amount of the germicide or other components in a solution according to the present invention refers to the amount formulated and introduced into the solution at the time the solution is made.

The present solution comprises at least one surfactant. Suitable surfactants can be either amphoteric, cationic, anionic, or nonionic which may be present (individually or in combination) in amounts up to 15 percent, preferably up to 5 percent weight by volume (w/v) of the total composition (solution). Preferred surfactants are amphoteric or nonionic surfactants, which when used impart cleaning and conditioning properties. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available under the trademark Tween® 20), polyoxyethylene (23) lauryl ether (Brij® 35), polyoxyethyene (40) stearate (Myrj® 52), polyoxyethylene (25) propylene glycol stearate (Atlas® G 2612). One non-ionic surfactant in particular consisting of a poly(oxypropylene)-poly (oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Mich., under the registered trademark "Tetronic". An analogous of series of surfactants, suitable for use in the present invention, is the poloxamer series which is a poly(oxyethylene) poly(oxypropylene) block polymers available under the trademark "Pluronic" (commercially available form BASF).

Various other ionic as well as amphoteric and anionic surfactants suitable for in the invention can be readily ascertained, in view of the foregoing description, from *McCutcheon's Detergents and Emulsifiers*, North American Edition, McCutcheon Division, MC Publishing Co., Glen Rock, N.J. 07452 and the CTFA International *Cosmetic Ingredient Handbook,* Published by The Cosmetic, Toiletry, and Fragrance Association, Washington, D.C.

Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

The foregoing surfactants will generally be present in a total amount from 0.01 to 5.0 percent weight by volume (w/v), preferably 0.1 to 5.0 percent, and most preferably 0.1 to 1.5 percent.

It may also be desirable to include water-soluble viscosity builders in the solutions of the present invention. Because of their demulcent effect, viscosity builders have a tendency to enhance the lens wearer's comfort by means of a film on the lens surface cushioning impact against the eye. Included among the water-soluble viscosity builders are the cellulose polymers like hydroxyethyl or hydroxypropyl cellulose, carboxymethyl cellulose, povidone, polyvinyl alcohol, and the like. Such viscosity builders may be employed in amounts ranging from about 0.01 to about 4.0 weight percent or less. The present solutions may also include optional demulcents.

Preferably, the invention is formulated as a "multipurpose solution," meaning that the solution may be used for cleaning, chemical disinfection, storing, and rinsing a contact lens. A multi-purpose solution preferably has a viscosity of less than 75 cps, preferably 1 to 50 cps, and most preferably 1 to 25 cps and is preferably is at least 95 percent weight by volume water in the total composition.

As stated, contact lenses are cleaned by contacting the lens with the subject aqueous solution. Although this may be accomplished by simply soaling a lens in the subject solution, greater cleaning can be achieved if a few drops of the solution are initially placed on each side of the lens, and the lens is rubbed for a period of time, for example, approximately 20 seconds. The lens can then be subsequently immersed within several milliliters of the subject solution. Preferably, the lens is permitted to soak in the solution for at least four hours. Furthermore, the lens is preferably rinsed with fresh solution after the rubbing step and again after being immersed within the solution. The aqueous solutions of the present invention are especially useful for soft contact lenses, with or without further additives. Nevertheless, the solutions of the present invention may be formulated into specific contact lens care products, such as wetting solutions, soaking solutions, cleaning and conditioning solutions, as well as multi-purpose type lens care solutions, etc. and mixtures thereof. Finally, such solutions can be applied to the lenses outside the eye or while on the eye, for example, in the form of droplets.

The aqueous solutions according to the present invention can be effectively used in disinfecting contact lenses by any of the well recognized methods. The lenses may be treated by the "cold" soaking method at room temperature for a period ranging from about 5 minutes to about 12 hours. The lenses are then removed from the solution, rinsed with the same or a different solution, for example a preserved isotonic saline solution and then replaced on the eye.

As indicated above, contact-lens wearers are commonly required to digitally or manually rub the contact lenses (typically between a finger and palm or between fingers) during daily cleaning and/or disinfecting of contact lenses. In one embodiment of the present invention, a method is provided in which rubbing is not required during treatment with the claimed specified solution, between removal from the eye and replacement of the lens following lens care. In a preferred embodiment of such a method, a soft lens is disinfected or both disinfected and cleaned with a multipurpose solution or an effective multipurpose solution that is the only daily solution needed for treating the lens outside the eye. Thus, in one embodiment of a method according to the invention, the described solution is used to treat a contact lens without rubbing, by a method comprising:

(a) soaking the contact lens that has not been rubbed with the solution for a specified time period, and (b) direct placement of the treated contact lens on the eye of the wearer.

Typically, step (a) may involve immersing the contact lens in the solution. Soaking may optionally comprise shaking or similarly agitating a container of the solution by manual means. Preferably, step (a) involves a period of soaking the contact lens in a container wherein the contact lens is completely immersed in the solution. By the term "direct placement" is herein meant that the solution is not diluted or rinsed off the lens with a different contact-lens solution prior to "insertion" or placement on the eye. In a particularly preferred embodiment, the method uses a product that is formulated as a multi-purpose or effective multi-purpose solution, wherein no other solution or product is required for daily cleaning of the lens, with the possible exception of an enzyme cleaner.

In yet another embodiment of a method according to the present invention, the claimed solution is used to clean a frequent replacement lens (FRL) that is planned for replacement after not more than about three months of use in the eye, or that is planned for replacement after not more than about 30 days of use in the eye, or that is planned for replacement after not more than about two weeks in the eye. Preferably, the lens is made from a polymer comprising about 0.0 to 5 mole percent repeat units derived from methacrylic acid (MAA), 10 to 99 mole percent of repeat units derived from hydroxyethyl methacrylate, and about 0.5 to 5 mole percent of cross-linking repeat units. Cross-linking repeat units may be derived, for example, from such monomers as ethyleneglycol dimethacrylate, divinylbenzene, and trimethylpropane trimethacrylate.

As an illustration of the present invention, several examples are provided below. These examples serve only to further illustrate aspects of the invention and should not be construed as limiting the invention.

EXAMPLE 1

An example of a preferred formulation of the subject invention is provided below TABLE 1

TABLE 1

| Constituent | mg/g | % W/W |
|---|---|---|
| Polyhexamethylene biguanide HCl (as a 20% w/w solution available under the mark Cosmocil ® CQ, from ICI Chemical Co.) | 0.0008 | 0.00008 |
| Alexidine | 0.002 | 0.0002 |
| Boric Acid | 8.30 | 0.830 |
| Sodium Phosphate (dibasic) | 3.10 | 0.310 |
| Sodium Chloride | 3.75 | 0.375 |
| Poloxamine (Tetronic ® 1107 from BASF Co.) | 10.00 | 1.000 |
| Tetrasodium phosphonate (as a 30% (w/w) solution available under the mark DeQuest ®2016 from Monsanto Co.) | 1.000 | 0.100 |
| Sodium Carbonate | 1.00 | 0.100 |
| Sodium Hydroxide, 1N and/or Hydrochloric Acid | as required for pH adjustment | as required for pH adjustment |
| Purified Water | Balance to 100 | |

This solution was prepared by weighing out the necessary amount of the ingredients, including sodium carbonate, the tetrasodium salt of 1-hydroxyethylidene-1,1-diphosphonic acid (also referred to as tetrasodium etidronate), commercially available as DeQuest ® 2016 from Monsanto (St. Louis, Mo.) into a glass beaker. The solution is prepared by gradually heating 80 percent of the water to 80° C. while dissolving the phosphonate and the buffer substances. The sodium chloride and carbonate is then added to the solution and dissolved, followed by the addition of surfactant. After the solution is cooled to room temperature, the alexidine and the PHMB as solutions are added through a sterile filter, followed by the balance of the PHMB. The pH of the resulting solution was about 7.3 to 7.5. (If necessary, the pH of the solution may be adjusted by use of an appropriate amount of hydrochloric acid or sodium hydroxide, as indicated in Table 1).

EXAMPLE 2

This example illustrates the comparable and enhanced cleaning efficacies of various compositions according to the present invention. A number of soft hydrogel lenses (FDA group IV, etafilcon A, lenses with 58% water content) were coated with protein deposits followed by treatment with one of several test solutions. The formulations of these test solutions are given in Table 2 below. The lenses were treated by means of an in-vitro protein deposit procedure as follows. An aqueous electrolyte solution was prepared, which solution consisted of approximately 0.70% sodium chloride, 0.17% potassium chloride, 0.22 percent sodium bicarbonate, and 0.0005% of calcium chloride, dihydrate. The electrolyte solution was prepared by adding the chlorides and bicarbonate to approximately 90% of the total volume of distilled water required, followed by thorough mixing of the solution. The pH was measured and, if necessary, adjusted to 7.2 +/−0.1 with either 1N HCl or 1N NaOH. The solution osmolality was between 280 and 320 mOsm/kg. An appropriate amount of the protein lysozyme was then added to the electrolyte solution so that the solution had a 0.2 percent concentration of lysozyme. The resulting solution was mixed for approximately thirty minutes at moderate speed. The pH was measured (and if necessary, adjusted to 7.2 +/−0.1 with either 1N HCl or 1N NaOH). A borate buffered saline solution was also prepared, comprising approximately 0.85% boric acid, 0.09% sodium borate, and 0.45 of sodium chloride. The pH was measured (and if necessary, adjusted to 7.2 +/−0.1 with either 1N HCl or 1N NaOH). The osmolality of the solution was between 280 to 320 mOsm/kg.

Protein deposits were deposited on a number Surevu® hydrogel lenses by placing each lens within a glass vial followed by submerging the lenses in approximately 5 ml of the electrolyte (protein-containing) solution. The vials were then capped and subjected to shaking at 40 rpms in a thermal water bath at approximately 37° C. for about sixty minutes. Subsequently, the lenses were allowed to be gently rinsed with the borate buffered saline to remove any loosely bound protein.

Once subjected to protein deposits, the lenses were then subjected to treatment with one of the subject solutions in Table 2 below. Treatment with the subject solutions consisted of placing the lens into approximately 5 ml of test solution for four hours to overnight. The lenses were then rinsed with a borate buffered saline.

Following the above-described treatment, the lenses were evaluated using UV assay at 280 nm to determine the amount of protein removed as a result of treatment. The results of this evaluation are provided in Table 3 below in which the relative protein removal for each formulation (n=4) is indicated as a percent change in total protein content compared with a Control solution consisting of borate buffered saline (BBS) solution.

TABLE 2

| Formulation | Ingredients |
|---|---|
| Comparative A | 4 ppm Alexidine and phosphate-borate buffer. |
| Comparative B | 0.8 ppm PHMB, 2 ppm Alexidine, 1% Tetronic ® 1107 poloxamine surfactant, and phosphate-borate buffer. |
| Comparative C | 0.8 ppm PHMB, 2 ppm Alexidine, 1% Tetronic ® 1107 poloxamine surfactant, 0.1% Dequest ® phosphonate, and phosphate-borate buffer. |
| D | 0.8 ppm PHMB, 2 ppm Alexidine, 0.2% Sodium Bicarbonate, 1% Tetronic ® 1107 poloxamine surfactant, 0.1% Dequest ® phosphonate, and phosphate-borate buffer. |
| E | 0.8 ppm PHMB, 2 ppm Alexidine, 0.2% Sodium Carbonate, 1% Tetronic ® 1107 poloxamine surfactant, 0.1% Dequest ® phosphonate, and phosphate-borate buffer. |

TABLE 3

| Formulation | Cleaning Efficacy (%) |
|---|---|
| A | 16% |
| B | 17% |
| C | 18% |
| D | 30% |
| E | 27% |

As is shown by the data provided in Table 3 above, taking the average for each formulation, the subject solutions containing a carbonate or bicarbonate (Formulations D and E) provided better protein removal that the comparative formulations without the carbonate or bicarbonate compounds.

EXAMPLE 3

This example illustrates lipid/protein cleaning efficacies from silicone hydrogel (Type IV lens silicone hydrogel, 35 to 36% water content). The lenses were treated with artificial tear solution in a glass vial containing 1.5 mls of the artificial tear solution. The Artificial Tear Solution (ATS) used in the depositing on the lens was made based on modifications from the published deposition model of D. Mirejovsky et al., *Optometry and Vision Science*, Vol. 68, No. 11, pp. 858–864. The ATS contained a mixture of proteins and lipids (listed in Table 4 below) in the MOPS buffer. Once the changes to the ATS solution were made, studies were done to confirm that each of the lipid and protein components in the mixture bind to the lens.

TABLE 4

| Artificial Tear Components | Specific Components |
| --- | --- |
| Salts and Buffer | NaCl, KCl, $NaHCO_3$, $CaCO_3$ (dihydrate), $NaH_2PO_4$ $H_2O$, 3-(N-Morpholino)propar sulfonic acid |
| Lipids | Palmitic acid methyl ester, cholesteryl oleate, tripalmitin, L-α-PC-dimyristoyl |
| Proteins | Mucin, lactoferrin, HSA, lysozyme |

The lenses were placed in a 55° C. water bath for 48 hours with constant shaking. After deposition, the lenses were removed from the solution, rinsed with borate buffer saline and placed overnight in the test solution of Example 1 above (hands-off regimen) and a Control solution consisting of a borate buffered saline (BBS) solution. The lenses were then removed from the test solution, rinsed with borate buffer saline and cut in half for protein and lipid analysis (HPLC and GC analysis). The percent (%) Cleaning Efficacy for Protein and Lipid respectively was calculated by the following equation:

$$\% \text{ Cleaning Efficacy} = \frac{(\text{Avg. deposits on control} - \text{Avg. deposits on cleaned lens})}{\text{Avg. of control deposited lens}} * 100\%$$

Based on the above test, it was found that the cleaning efficacy of the test formulation was 100 percent.

EXAMPLE 4

This Example illustrates that the microbiocidal efficacy of solutions according to the present invention is not compromised. The antimicrobial efficacy of each of various formulations A-F in Example 2 above were evaluated. Microbial challenge inoculums were prepared using *Pseudomonas aeruginosa* (ATCC 9027), *Staphylococcus aureus* (ATCC 6538), *Serratia marcescens* (ATCC 13880), *Candida albicans* (ATCC 10231), and *Fusarium solani* (ATCC 36031). The test organisms were cultured on appropriate agar and the cultures were harvested using sterile DPBST (Dulbecco's Phosphate Buffered Saline plus 0.05% w/v polysorbate 80) or a suitable diluent and transferred to a suitable vessel. Spore suspensions were filtered through sterile glass wool to remove hyphal fragments. *Serratia marcescens*, as appropriate, was filtered (eg., through a 1.2 μfilter) to clarify the suspension. After harvesting, the suspension was centrifuged at no more than 5000×g for a maximum of 30 minutes at 20–25° C. The supernatant was poured off and resuspended in DPBST or other suitable diluent. The suspension was centrifuged a second time, and resuspended in DPBST or other suitable diluent. All challenge bacterial and fungal cell suspensions were adjusted with DPBST or other suitable diluent to $1 \times 10^7 - 10^8$ cfu/mL. The appropriate cell concentration may be estimated by measuring the turbidity of the suspension, for example using a spectrophotometer at a preselected wavelength, for example 490 nm. One tube was prepared containing a minimum of 10 mL of test solution per challenge organism. Each tube of the solution to be tested was inoculated with a suspension of the test organism sufficient to provide a final count of $1.0 \times 10^5 - 10^6$ cfu/mL, the volume of the inoculum not exceeding 1% of the sample volume. Dispersion of the inoculum was ensured by vortexing the sample for at least 15 seconds. The inoculated product was stored at 10–25° C. Aliquots in the amount of 1.0 mL were taken of the inoculated product for determination of viable counts after certain time periods of disinfection. The time points for the bacteria were, for example, 1, 2, 3, and 4 hours when the proposed regimen soaking time was 4 hours. Yeast and mold were tested at an additional timepoint of $\geq 16$ hours (4 times the regimen time). The suspension was mixed well by vortexing vigorously for at least 5 second. The 1.0 mL aliquots removed at the specified time intervals were subjected to a suitable series of decimal dilutions in validated neutralizing media. The suspensions were mixed vigorously and incubated for a suitable period of time to allow for neutralization of the microbial agent. The viable count of organisms was determined in appropriate dilutions by preparation of triplicate plates of trypticase soy (TSA) agar for bacteria and Sabouraud dextrose agar (SDA) for mold and yeast. The bacterial recovery plates were incubated at 30–35° C. for 2–4 days. The yeast was incubated at 20–30° C. for 2–4 days and mold recovery plates at 20–25° C. for 3–7 days. The average number of colony forming units was determined on countable plates. Countable plates refer to 30–300 cfu/plates for bacteria and yeast, and 8 to 80 cfu/plate for mold except when colonies are observed only for the $10^0$ or $10^{-1}$ dilution plates. The microbial reduction was then calculated at the specified time points. In order to demonstrate the suitability of the medium used for growth of the test organisms and to provide an estimation of the initial inoculum concentration, inoculum controls were made by dispersing an identical aliquot of the inoculum into a suitable diluent, for example DPBST, using the same volume of diluent used to suspend the organism as listed above. Following inoculation in a validated neutralizing broth and incubation for an appropriate period of time, the inoculum control must be between $1.0 \times 10^5 - 1.0 \times 10^6$ cfu/mL The solutions were evaluated based on the performance requirement referred to as the "Stand-Alone Procedure for Disinfecting Products" (hereafter the "stand-alone test") and is based on the Disinfection Efficacy Testing for contact lens care products under the Premarket Notification (510(k)) Guidance Document For Contact Lens Care Products dated May 1, 1997, prepared by the U.S. Food and Drug Administration, Division of Ophthalmic Devices. This performance requirement does not contain a rub procedure. This performance requirement is comparable to current ISO standards for disinfection of contact lenses (revised 1995). The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per niL must be reduced by a mean value of not less than 3.0 logs within the given disinfection period. The number of mold and yeast recovered per mL must be reduced by a mean value of not less than 1.0 log within the minimum recommended disinfection tine with no increase at four times the minimum recommended disinfection time.

The formulations tested are listed in Table 2 and the test results are shown in Table 5.

TABLE 5

| PRODUCT | | Compar. Formula A | Compar. Formula B | Compar. Formula C | Formula D | Formula E |
|---|---|---|---|---|---|---|
| *Staphylococcus* | 30 Minutes | 4.9 | 3.9 | >4.9 | 4.9 | 3.8 |
| *aureus* | 1 Hour | >4.9 | >4.9 | >4.9 | 4.9 | >4.9 |
| | 2 Hours | >4.9 | >4.9 | >4.9 | >4.9 | >4.9 |
| | 3 Hours | >4.9 | >4.9 | >4.9 | >4.9 | >4.9 |
| | 4 Hours | >4.9 | >4.9 | >4.9 | >4.9 | >4.9 |
| *Pseudomonas* | 30 Minutes | >4.7 | 3.9 | 4.4 | 4.7 | 3.7 |
| *aeruginosa* | 1 Hour | >4.7 | >4.7 | >4.7 | >4.7 | >4.7 |
| | 2 Hours | >4.7 | >4.7 | >4.7 | >4.7 | >4.7 |
| | 3 Hours | >4.7 | >4.7 | >4.7 | >4.7 | >4.7 |
| | 4 Hours | >4.7 | >4.7 | >4.7 | >4.7 | >4.7 |
| *Serratia* | 30 Minutes | 3.1 | 3.6 | 4.5 | 3.3 | 3.9 |
| *marcescens* | 1 Hour | >4.8 | >4.8 | >4.8 | >4.8 | >4.8 |
| | 2 Hours | >4.8 | >4.8 | >4.8 | >4.8 | >4.8 |
| | 3 Hours | >4.8 | >4.8 | >4.8 | >4.8 | >4.8 |
| | 4 Hours | >4.8 | >4.8 | >4.8 | >4.8 | >4.8 |
| *Candida* | 30 Minutes | 3.8 | 3.0 | 3.1 | 3.5 | 3.2 |
| *albicans* | 1 Hour | 4.7 | 4.3 | 4.1 | >4.7 | 4.6 |
| | 2 Hours | >4.7 | >4.7 | >4.7 | >4.7 | >4.7 |
| | 3 Hours | >4.7 | >4.7 | >4.7 | >4.7 | >4.7 |
| | 4 Hours | >4.7 | >4.7 | >4.7 | >4.7 | >4.7 |
| | 24 Hours | >4.7 | >4.7 | >4.7 | >4.7 | >4.7 |
| *Fusarium* | 30 Minutes | 3.0 | 3.1 | 2.4 | 2.6 | 2.2 |
| *solani* | 1 Hour | 3.8 | 3.8 | 3.3 | 3.5 | 3.6 |
| | 2 Hours | >4.6 | 4.6 | 4.6 | >4.6 | 4.4 |
| | 3 Hours | 4.5 | >4.6 | >4.6 | >4.6 | 4.5 |
| | 4 Hours | 4.6 | >4.6 | >4.6 | >4.6 | 4.6 |
| | 24 Hours | >4.6 | >4.6 | >4.6 | >4.6 | >4.6 |

These results show that the microbicidal efficacy of the solutions containing carbonate or bicarbonate (formulations D and E), in combination with one or more biguanide disinfecting agents, were not compromised compared to comparative formulations not containing a carbonate for enhanced cleaning.

While the invention has been described in conjunction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

What is claimed is:

1. A method of disinfecting or cleaning and disinfecting a soft contact lens with a multi-purpose solution or effective multipurpose solution, which method comprises:
   (a) soaking the lens in an ophthalmically safe solution, such that acceptable disinfection of the contact lens is obtained within a minimum recommended soaking period, the solution comprising, in formulation, the following components:
      (i) 0.010 to 1.0 percent by weight of the solution of an alkali metal carbonate or bicarbonate salt;
      (ii) an effective amount of a buffering system comprising one or more non-carbonate buffers which non-carbonate buffers provide a buffering capacity of 0.01 to 0.5 nM of 0.01 N of HCl and 0.01 to 0.3 of 0.01 N of NaOH to change the pH one unit;
      (iii) an effective amount of a non-ionic surfactant;
      (iv) an effective amount of at least one germicide; and
   (b) directly placing the treated lens on the eye of the wearer, such that (i) rinsing with a different solution prior to placement on the eye is not generally required, and (ii) no other solution is generally required for daily cleaning of the lens.

2. The method of claim 1 comprising the sequential steps of rubbing the lens with the solution, followed by immersing the lens within the solution.

3. The method of claim 1 wherein the method provides complete cleaning of the lens such that digital rubbing of the lens is not necessary to clean the lens.

4. The method of claim 1 wherein the antimicrobial agent is a biguanide compound or polymer.

5. The method of claim 4, wherein the antimicrobial agent is selected from the group consisting of polymeric biguanides and bis(biguanides), salts of the foregoing, and combinations thereof.

6. The method of claim 1 wherein the solution has a pH from about 6 to about 8 and an osmolality of between about 250 to 350 mOsm/kg.

7. The method of claim 1, wherein the carbonate is selected from the group consisting of sodium bicarbonate, sodium carbonate, potassium carbonate, potassium bicarbonate, and mixtures thereof.

8. The solution of claim 1, wherein the buffers are selected from the group consisting of borates, citrates, TRIS, $M_2HPO_4$, $MH_2PO_4$ and $MH_2PO_4$ wherein M is an alkali metal, and mixtures thereof.

9. The method of claim 1, wherein the buffer system comprises buffers selected from the group consisting of borate buffers, phosphate buffers, and mixtures thereof.

10. An aqueous solution having a pH from about 5 to about 8 for treating contact lenses comprising:
   (a) 0.010 to 1.0 percent by weight of the solution of an alkali metal carbonate or bicarbonate salt;
   (b) an effective amount of a buffering system comprising one or more non-carbonate buffers which non-carbonate buffers provide a buffering capacity of 0.01 to 0.5 mM of 0.01 N of HCl and 0.01 to 0.3 of 0.01 N of NaOH to change the pH one unit;
   (c) an effective amount of a non-ionic surfactant; and
   (d) an effective amount of at least one germicide.

11. The solution of claim 10 wherein the antimicrobial agent is a biguanide compound or polymer.

12. The solution of claim 11, wherein the antimicrobial agent is selected from the group consisting of polymeric biguanides and bis(biguanides), salts of the foregoing, and combinations thereof.

13. The solution of claim 10 wherein the solution has a pH from about 6 to about 8 and an osmolality of between about 250 to 350 mOsm/kg.

14. The solution of claim 10, wherein the carbonate is selected from the group consisting of sodium bicarbonate, sodium carbonate, potassium carbonate, potassium bicarbonate, and mixtures thereof.

15. The solution of claim 10, wherein the buffer system comprises buffers selected from the group consisting of borate buffers, phosphate buffers, and mixtures thereof.

16. The solution of claim 10, wherein the buffers are selected from the group consisting of borates, citrates, TRIS, $M_2HPO_4$, $MH_2PO_4$ and $MH_2PO_4$ wherein M is an alkali metal, and mixtures thereof.

17. An aqueous solution having a pH from about 5 to about 8 for treating contact lenses
 (a) 0.010 to 1.0 percent by weight of the solution of an alkali metal carbonate or bicarbonate salt; and
 (c) an effective amount of a non-ionic surfactant;
 (d) an effective amount of at least one biguanide germicide.
 (e) an effective amount of a buffer system comprising one or more buffers selected form the group consisting of phosphate and borate buffers and mixtures thereof, which buffers provide a buffering capacity of 0.01 to 0.5 mM of 0.01 N of HCl and 0.01 to 0.3 of 0.01 N of NaOH to change the pH one unit.

18. A method of disinfecting or cleaning and disinfecting a soft contact lens with a multi-purpose solution or effective multipurpose solution, which method comprises:
 (a) soaking the lens in an ophthalmically safe solution, such that acceptable disinfection of the contact lens is obtained within a minimum recommended soaking period, the solution comprising, in formulation, the following components:
  (i) 0.010 to 1.0 percent by weight of the solution of an alkali metal carbonate or bicarbonate salt;
  (ii) an effective amount of a buffering system comprising at least one phosphate buffer and at least one borate buffer to provide a buffering capacity of 0.01 to 0.5 mM of 0.01 N of HCl and 0.01 to 0.3 of 0.01 N of NaOH to change the pH one unit;
  (iii) an effective amount of a non-ionic surfactant;
  (iv) an effective amount of alexidine germicide; and
 (b) directly placing the treated lens on the eye of the wearer, such that (i) rinsing with a different solution prior to placement on the eye is not generally required, and (ii) no other solution is generally required for daily cleaning of the lens.

* * * * *